(12) United States Patent
Alessandri

(10) Patent No.: US 6,514,199 B1
(45) Date of Patent: Feb. 4, 2003

(54) TELECOMMUNICATION SYSTEM FOR EXCHANGING PHYSIOLOGICAL STATE INFORMATION BETWEEN A PHYSICAL PERSON AND AN INFORMATION SYSTEM

(75) Inventor: Nerio Alessandri, Longiano (IT)

(73) Assignee: Technogym S.r.l., Gambettola (IT)

( * ) Notice: Subject to any disclaimer, the term of this patent is extended or adjusted under 35 U.S.C. 154(b) by 0 days.

(21) Appl. No.: 09/550,339

(22) Filed: Apr. 14, 2000

(30) Foreign Application Priority Data

Apr. 16, 1999 (IT) .......................................... B099A0179

(51) Int. Cl.⁷ ............................ A61B 5/00; H04M 11/00
(52) U.S. Cl. ...................... 600/300; 455/403; 128/903; 128/904; 235/462.01; 482/8
(58) Field of Search ................................ 600/300–301, 600/529–538, 544–545, 500, 481–486, 558, 559; 128/903–904, 920, 898, 924, 925; 705/2–4; 702/9, 19; 482/8, 9; 235/462.01

(56) References Cited

U.S. PATENT DOCUMENTS

| | | | | |
|---|---|---|---|---|
| 4,952,928 A | * | 8/1990 | Carroll et al. ............... 128/898 |
| 5,527,239 A | * | 6/1996 | Abbondanza ................. 482/8 |
| 5,546,943 A | | 8/1996 | Gould | |
| 5,890,997 A | * | 4/1999 | Roth ............................. 482/8 |
| 5,947,868 A | * | 9/1999 | Dugan ......................... 482/8 |
| 5,954,640 A | * | 9/1999 | Szabo ......................... 600/300 |
| 6,159,147 A | * | 12/2000 | Lichter et al. ............... 600/300 |
| 6,231,519 B1 | * | 5/2001 | Blants et al. ................ 600/300 |
| 6,295,506 B1 | * | 9/2001 | Heinonen et al. ........... 702/104 |
| 6,379,301 B1 | * | 4/2002 | Worthington et al. ........ 600/309 |

FOREIGN PATENT DOCUMENTS

| | | |
|---|---|---|
| EP | 710 465 A1 | 5/1996 |
| IT | B094A 000440 | 10/1994 |
| WO | 97/11753 | 4/1997 |

* cited by examiner

*Primary Examiner*—Max F. Hindenburg
*Assistant Examiner*—Michael Astorino
(74) *Attorney, Agent, or Firm*—Arent Fox Kintner Plotkin & Kahn

(57) ABSTRACT

A telecommunication system for exchanging information concerning personalized parameters of physiological state between a physical person and an information system comprises measuring means for measuring physiological parameters of the physical person; and processing means interconnected with the measuring means and with the information system, for transmitting to the information system at least input signals corresponding to the physiological parameters acquired by the person and for transmitting to the physical person output information corresponding to those received in return from the information system. The telecommunication system allows a dialogue between the physical person and the information system to control his/her own physical condition in a scientifically accurate and personalized manner.

32 Claims, 2 Drawing Sheets

TELECOMMUNICATION SYSTEM FOR EXCHANGING PHYSIOLOGICAL STATE INFORMATION BETWEEN A PHYSICAL PERSON AND AN INFORMATION SYSTEM

BACKGROUND OF THE INVENTION

The present invention relates to the technical field of information systems in general which allow an exchange of information between a user and a data base or a network; in particular this system can be correlated to the fitness or wellness sector and integrated with exercise machines for training, re-educating and maintaining the well-being of the body.

Exercise machines of more modem and advanced conception, both professional and amateur-oriented, are designed in such a way as to allow the user to plan his/her physical activities in relation with his/her own personal characteristics and requirements.

For this purpose machines are known which, although conceived for a general employment able to meet the diversified demands of a plurality of users, can then be pre-set on each occasion as a function of each individual user and of the workout plan the user actually intends to follow. A personalized management system for this type of machined is, for instance, already known from the patent IT-1.274.053 in the name of the same Applicant.

SUMMARY OF INVENTION

The present invention more particularly relates to a telecommunication system which extends beyond the physical borders of a gym or of a physical education venue in general, and has the fundamental aim of allowing a further advancement of the individual management of physical activities and a more advanced and accurate personalization so as to take into consideration the person's actual physiological conditions, enabling to take into account also a series of other parameters such as those concerning his/her nutrition and those concerning the energy consumption linked with that person's actual daily lifestyle.

According to the invention this aim is achieved by a telecommunication system for exchanging information concerning physiological state parameters between a physical person and an information system, comprising measuring means for measuring physiological parameters directly from the physical person; and processing means interconnected with the measuring means and with the information system to transmit to the information system at least input signals corresponding to the acquired physical parameters and to transmit to the physical person output information corresponding with those received in return from the information system.

The invention allows the quantification and the scientifically planned graduation of the workload as a function of the measurement and processing of a set of physiological parameters which are significant for representing the physical condition of the user and whose control allows in the first place to monitor the reaching of reference or target thresholds of each individual users.

If the system comprises a terminal that allows the user to interface with the processing means, to enter personal and specific data therein, the user's activity can also be planned as a function of other information wherefrom it is possible, for instance, to deduce: the energetic content stored with daily nutrition or referable to a different time interval; and/or the portion of energy content dissipated through the user's work activity. All this to allow to manage the user's physical activity on the exercise machine in a personalized, rational manner as a function of a realistic energy budget. Similarly with regard to the management of diets, nutrition, linked to the aforesaid physical activities or otherwise.

The terminal can allow the user to connect also to the information system both locally and remotely. It can be connected to the information system by means of a fixed physical network; or, if the terminal comprises for instance a radiotelephone, it can allow the wireless exchange of information between the user and the information system. In either case the exchange of information is easy, immediate and possible on a global and planetary scale.

Providing the terminal with appropriate interface means, such as a board with miniaturized circuitry, in addition to the acquisition of information from the information system it is also possible to store signals which can allow to query the data base or the network or to configure in a personalized and automated manner the exercise machines of the gym normally attended by the user or any other gym he/she may desire to access, for instance when staying in a location more or less distant from his/her habitual residence.

Naturally, the aforesaid personalization of the configuration of the machines is not limited to exercise machines, but can be extended also to electrical appliances or to machines finding more general employment whose functionalities allow, for instance, to interact in the broadest sense of the term with the physical well-being of the user and/or with his/her energy exchanges with the surrounding environment.

If the system according to the invention is provided with suitable communication software constituted for instance by a standard operating system such as Windows®CE, the telecommunication system according to the invention can advantageously interconnect with local area networks such as intranets or with the global network, the Internet, and dialogue with data bases, with processing centers or intelligent software systems able to manage incoming and output information about person's physical condition, physical activities and/or medical scientific information connectable thereto.

To assure on the one hand the confidentiality of the data and on the other the security of a specific personalization, the system can advantageously be equipped also with means for recognizing the person embodied for instance by means of a fingerprint reader or a retinal image reader.

BRIEF DESCRIPTION OF THE DRAWINGS

The technical features of the invention, according to the aforesaid aims, can clearly be noted from the content of the claims set out below and its advantages shall become more readily apparent in the detailed description that follows, made with reference to the accompanying drawings, which represent an embodiment provided purely by way of non-limiting example, in which:

DESCRIPTION OF THE PREFERRED EMBODIMENT

Figure 1:
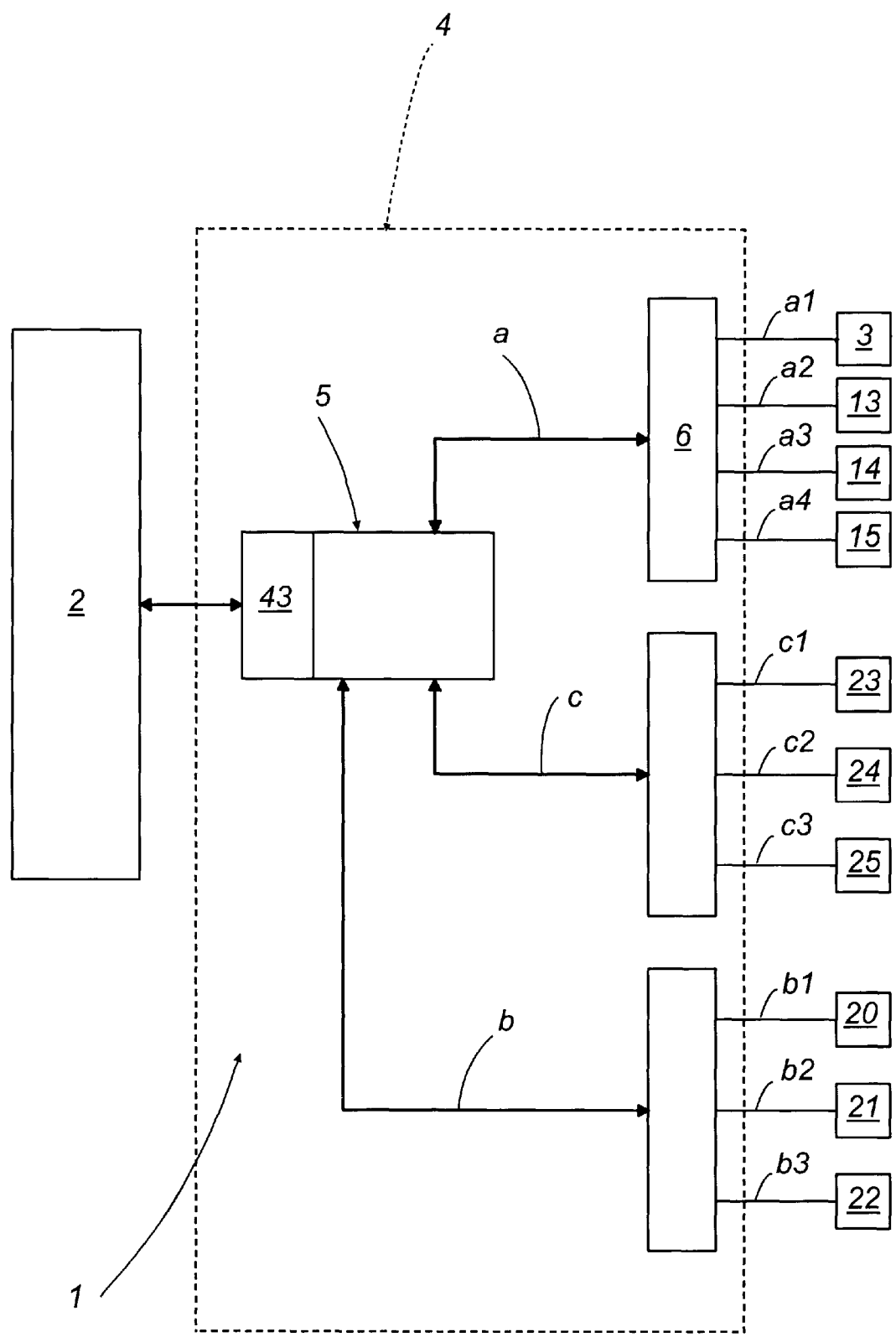
FIG. 1 is a schematic block function representation of the telecommunication system according to the invention.

With reference to the accompanying drawings, the number 1 indicates in its entirety a telecommunication system for exchanging information concerning personal physiological state parameters between a physical person and an information system 2.

The system 1 essentially comprises measuring means 3, such as a cardiac frequency meter, for measuring directly from the physical person physiological parameters significant for monitoring his/her physical condition; and processing means 4 which include a software for processing and handling information pertaining to physiological condition parameters of the person and which are interconnected with the measuring means and with the information system 2, to transmit to the information system 2 this information in the form of input signals a1 and to transmit to the physical person output information b, c corresponding with that received in return from the information system 2.

The processing means 4 [FIG. 1] comprise a microprocessor device 5, a terminal 6 and first interface means 7, 8, 9, 10. The microprocessor device 5 is provided with a central processing unit CPU; with means 40, 41, 42 for storing data, programs and information for external peripheral units, and with a signal modulation and demodulation unit—modem 43.

Figure 2:
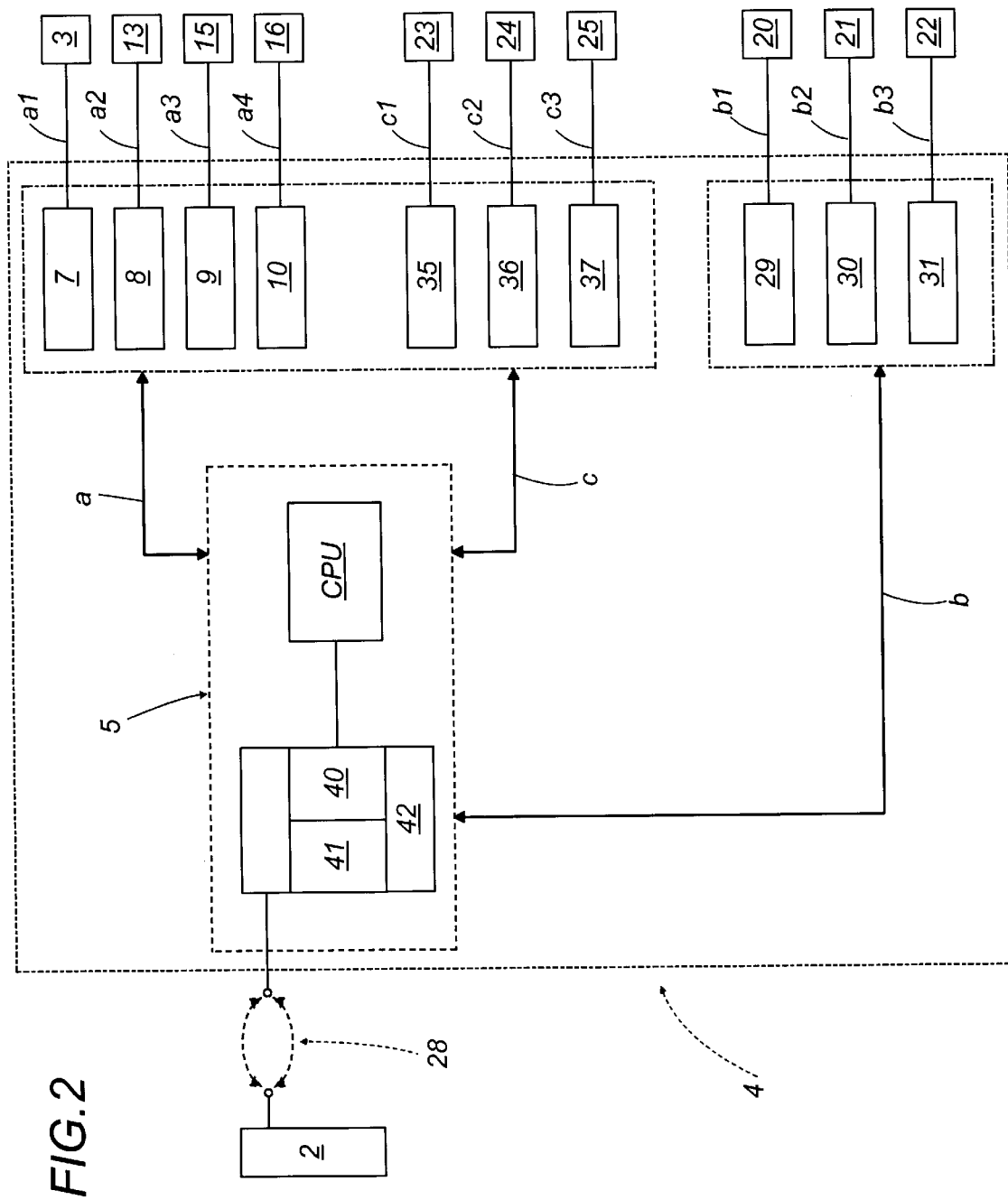
FIG. 2 is a detailed block function representation of a variation in the execution of the system of FIG. 1.

The terminal 6 is preferably of the portable, palmtop type and it is integrated in a single body with the microprocessor device 5. Moreover, according to an alternative embodiment, shown in FIG. 2, it comprises a radiotelephone which allows the person to be connected with the information system 2 according to a wireless mode.

The interface means 7, 8, 9, 10 are interconnected with the measuring means 3 and can be interconnected with an input device 13 and with means 15, 16 for identifying the person. The input device 13 can be embodied by a keyboard or by a barcode reader. The means 15, 16 for identifying the person can be embodied by a fingerprint reader and/or also by a retinal image reader.

The first interface means 7, 8, 9, 10 in combination with the microprocessor device 5 allow to enter into the information system 2, and through the first interface means 7, 8, 9, 10 and the microprocessor device 5, information that is understandable for the operating system suitably converting the signals 1a of the measuring means 3 and of the information a2, a3, a4 entered by the person by means of the input device 13 and/or through identification means 15, 16.

Clearly, the information that can be entered into the information system 2 can be the most disparate, as it is easy to understand that through the keyboard the physical person can enter the most widely varied information establishing, through the software that equips the processing means 4, a veritable dialogue with the information system 2. The insertion of information through the bar code reader can allow to send to the information system 2, in a rapid and complete manner, information for instance on the nature, quality and quantity of food products consumed by the user with his/her daily nutrition; information which can then be processed by the information system 2 for a whole series of diet and energy information which can be both aimed at informing the physical person or at being exploited to quantify and modulate the workload needed by the physical person to work them off.

For the communication to the physical person of the data b1, b2, b3 processed by the information system 2, the processing means 4 can be provided with an output device 20, 21, 22 interconnected with related second interface means 29, 30, 31. The output device can present the most disparate embodiments and can be embodied for instance by a video 20, by a display 21, by a printer 22 and can lastly be integrated in the same processing means 4 and, more in particular in the portable terminal 6 or even in the radiotelephone itself which an integrate in a single body also the second interface means 29, 30, 31 themselves.

The processing means 4 also comprise third interface means 35, 36, 37 connected with an output device 23, 24 which receives from the information system 2 information in the form of appropriately processed signals c1, c2, c3. The third interface means 35, 36, 37 can be integrated in the same portable terminal 6 or even in the radiotelephone. The output device connected thereto can assume a broad range of concrete embodiments, represented by way of non limiting example by a board 23 with miniaturized circuitry able to store said signals c1, c2, c3; or by a directly connected machine 24, 25 whose functionalities can be modulated according to the person's physiological parameters.

The board 23 can be of the kind employed by the system for managing the personalization of exercise machines already subjected to patent protection by the same Applicant, and can allow the physical person to store through the communication system 1 the signals which will be necessary for configuring the exercise machines when the physical person accesses his/her own gym.

Naturally, through portable processing means 4 it is possible to connect to the operating system 2 the exercise machine 24 of one's own gym or in general any other electrical appliance 25 able to interact energetically with the person and to download in real time from the operating system 2 the configuration parameters necessary for personalizing the machine 24, 25.

As to the information system 2, from the above description one can observe that it can include a computerized data base and/or even the software for processing the physical person's own personal data as well as data contained n the data base. Moreover, the information system 2 can reside within a local computer or otherwise can be contained in a remote server reachable by the processing means 4 through a telecommunication and information network 28 which can be local, remote, fixed or wireless like those currently employed for mobile telephony. Interactivity with the network 28 shall be enabled by providing the processing means 4 with suitable software, for instance of the Windows®CE type, which is found to be particularly well suited to equip portable, palmtop processing means 4.

The invention thus conceived can be subject to numerous modifications and variations, without thereby departing from the scope of the inventive concept. Moreover, all components can be replaced by technically equivalent elements.

What is claimed is:

1. A telecommunication system for exchanging information concerning personalized state parameters between a physical person and an information system having at least an energy intake information of the physical person, the telecommunication system comprising:

measuring means for measuring physiological parameters from the physical person;

processing means interconnected with the measuring means and with the information system for processing input signals, corresponding to the physiological parameters acquired from the person, and output information, in the form of data coming from the information system; said processing means presenting at least a first interface means, for transmitting to the information system the input signals corresponding to the physiological parameters acquired from the person, and a second interface means, for at least a data output device provided to transmit to the person information in the form of data coming from the information system;

wherein said processing means further includes at least a third interface means for sending information, in the form of signals processed by the processing means based on information coming from the information system, to a machine interacting with the person's energy exchanges with the surrounding environment and having functionalities which can be selectably modulated as a function of at least the energy intake information from the information system and the person's physiological parameters.

2. A system as claimed in claim 1, wherein the measuring means comprises at least a cardiac sensor for monitoring the person's physical condition.

3. A system as claimed in claim 1, wherein the processing means further comprises:

a microprocessor device; and a terminal;

wherein the terminal, the at least first interface means and the measuring means are interconnected to each other.

4. A system as claimed in claim 3, wherein the terminal is a portable palmtop device.

5. A system as claimed in claim 4, wherein the terminal and the microprocessor device are integrated in a single body.

6. A system as claimed in claim 3, wherein the terminal includes a radiotelephone.

7. A system as claimed in claim 3, comprising a data input device connected to said at least first interface means, through which the person sends information in the form of data to the processing means.

8. A system as claimed in claim 7, wherein the data input device includes a keyboard.

9. A system as claimed in claim 7, wherein the input device includes a barcode reader.

10. A system as claimed in claim 1, comprising means for personally identifying the person.

11. A system as claimed in claim 10, wherein the personal identification means includes a reader of the person's fingerprint.

12. A system as claimed in claim 10, wherein the personal identification means includes a reader of the person's retinal image.

13. A system as claimed in one of the claims from 10 to 12, wherein said at least first interface means are functionally interconnected with the personal identification means to send to the information system corresponding input information coming from the person.

14. A system as claimed in claim 1, wherein the output of the output device is a video.

15. A system as claimed in claim 1, wherein the output device is a display.

16. A system as claimed in claim 1, wherein the output device is a printer.

17. A system as claimed in one of claims 1, 14, 15, or 16, wherein the output device is integrated with the processing means.

18. A system as claimed in claim 16, wherein the terminal is portable.

19. A system as claimed in claim 1, wherein the processing means include a terminal incorporating at least the second interface means for the data output device.

20. A system as claimed in claim 19, wherein the terminal includes a radiotelephone.

21. A system as claimed in claim 1, wherein the processing means further comprises:

a terminal provided with said third interface means.

22. A system as claimed in claim 21, wherein the terminal is portable.

23. A system as claimed in claim 22, wherein the terminal includes a radiotelephone.

24. A system as claimed in claim 1, wherein said at least third interface means comprises a board with miniaturized circuitry able at least to store said signals.

25. A system as claimed in claim 1, wherein said machine is an exercise machine.

26. A system as claimed in claim 1, wherein the machine is an electrical appliance interacting with the physical person.

27. A system as claimed in claim 1, wherein the information system includes a computerized data base.

28. A system as claimed in claim 27, wherein the information system is locally connected with the user.

29. A system as claimed in claim 27, wherein the information system is remote from the user with whom it is connected by means of a telecommunications network.

30. A system as claimed in claim 29, wherein the processing means include a software for interactivity with the telecommunications network.

31. A system as claimed in claim 30, wherein the software for interactivity with the network is hand held computer software.

32. A system as claimed in claim 1, wherein the processing means includes a software for processing and managing information pertaining to the person's physiological state parameters.

* * * * *